United States Patent [19]

Krupey et al.

[11] 4,123,343

[45] Oct. 31, 1978

[54] PURIFICATION OF GLYCOPROTEINS AND IMMUNIZATION THEREWITH

[75] Inventors: John Krupey, Montreal; Ewald F. Welchner, LaSalle, both of Canada

[73] Assignee: American Home Products Corporation, New York, N.Y.

[21] Appl. No.: 806,562

[22] Filed: Jun. 14, 1977

[51] Int. Cl.² ............... G01N 27/26; G01N 33/16; C25B 7/00

[52] U.S. Cl. ............ 204/180 G; 204/299 R; 424/12

[58] Field of Search ........... 204/180 R, 180 S, 180 G, 204/299; 23/230 B; 424/12; 260/112

[56] References Cited

U.S. PATENT DOCUMENTS

| | | | |
|---|---|---|---|
| 2,705,696 | 4/1955 | Wolfe et al. | 424/12 |
| 3,410,839 | 11/1968 | DeCarvalho | 424/12 X |
| 3,704,282 | 11/1972 | Spector | 424/12 X |
| 3,789,116 | 1/1974 | Kay | 424/12 X |
| 3,791,950 | 2/1974 | Allington | 204/180 G |
| 3,799,863 | 3/1974 | Zeineh | 204/180 G X |
| 3,948,743 | 4/1976 | Monthony et al. | 204/180 G |
| 4,030,995 | 6/1977 | Starkweather | 204/180 G |
| 4,065,445 | 12/1977 | Bohn et al. | 424/12 X |

OTHER PUBLICATIONS

Pierce et al., "Biologically Active Hormones . . . Luteinizing Hormone", J. Biol. Chem., (Apr. 10, 1971), vol. 246, No. 7, p. 2321.
Donini et al., "Subunits of Human Chorionic Gonadotrophin . . . Study", Acta Endocrinologica, 73, (1973), pp. 133-145.
Morgan et al., "Nature of the Subunits of Human Chorionic Gonadotrophin", Endocrinology, vol. 88, p. 1045, (Apr. 1971).
Morgan et al., "Properties of the Subunits of Human Chorionic Gonadotropin", Endocrinology, vol. 94, No. 6, p. 1601, (1971).

Primary Examiner—Arthur C. Prescott
Attorney, Agent, or Firm—Adley F. Mandel

[57] ABSTRACT

A method is disclosed for the purification of the beta subunit of human chorionic gonadotrophin. Also disclosed is an antiserum composition and method of producing same using spleen immunization to obtain antiserum compositions having high antibody titers.

5 Claims, No Drawings

PURIFICATION OF GLYCOPROTEINS AND IMMUNIZATION THEREWITH

BACKGROUND OF THE INVENTION

Human chorionic gonadotrophin (hereinafter referred to as hCG) is composed of two subunits; the α subunit is largely identical to the α subunit of TSH, FSH and LH; the β subunit also possesses areas which are homologous with these glycoprotein hormones as well as a 30 amino acid sequence that is not homologous. Many preparations of the β subunit of hCG obtained by chromatography of urea dissociated hCG exhibit microheterogeneity, Domini et al, Acta Endocr. 73:133–145, 1973, i.e., they contain carbohydrate chains of different lengths and complexity. Besides other glcoprotein hormones or their metabolites, it is also possible that undisassociated hCG and subunit are present to some extent as contaminants in these preparations. These antigenic contaminants will thus also produce antibodies when injected along with the primary antigen in immunization procedures. It is therefore desirable to further purify the β-hCG prior to antibody production in order to produce a highly specific antiserum with low cross reactivity to interfering substances. Such an antiserum would make possible the design of more sensitive agglutination reactions with antigen sensitized carriers.

It was thought that gel electrophoresis would provide a suitable approach to obtain the desired, purified antigen. Such a procedure for the separation of human serum proteins is described by Davis in Ann. N.Y. Ac. Sci., 121:404-427(1964) herein incorporated by reference. But, the staining procedure for localizing the separated protein requires prior fixation of the protein in acid which causes complete denaturation of the protein. Hartman et al in Anal. Biochem. 30:391-39(1969) herein incorporated by reference attempted to provide a method of staining the electrophoresed protein with minimal denaturation by utilizing anilinonaphthalene sulfonate to stain the gels once they are removed form their tubes following electrophoresis. It has been found, however, that this latter procedure is unsatisfactory with hCG and no staining is observed. The further suggestion by Hartman to utilize HCl to intensify the stain is also counterproductive causing further denaturation of the protein.

SUMMARY OF THE INVENTION

The present invention relates to a method for purifying the beta subunit of human chorionic gonadotrophin which comprises subjecting the β-hCG subunit to polyacrylamide gel electrophoresis in tubes containing an upper gel and a lower gel suspended in an elctrophoretic apparatus having an upper tank buffer and a lower tank buffer wherein the upper tank buffer contains a fluorescent probe consisting of the magnesium salt of 8-anilino-1-naphthalene-sulfonic acid and a tracking dye, and, after terminating the electrophoretic run, cutting out the fluorescent boundaries corresponding to the β-hCG subunit. The invention also comprises the β-hCG produced by the above method.

This invention further comprises the antiserum obtained by immunizing a suitable host animal with the β-hCG. A preferred method for producing an antiserum comprises immunizing the host animal, usually rabbit, with an antigen in the spleen.

DETAILED DESCRIPTION OF THE INVENTION

Human chorionic gonadotrophin, a glycoprotein hormone is obtained by extraction from the urine of pregnant women in the first trimester of pregnancy. Following a crude purification, the two subunits are further purified and separated through a combination of ion exchange chromatography and sieve chromatography. In the last steps the alpha subunit is disassociated from the beta subunit in a 10M urea solution. The hCG/urea solution is then sieve chromatographed twice on a urea impregnated column. The purified subunits are eluted from the column, the urea removed and the products lyophilized.

The β-hCG obtained from the above described choromatographic procedures is then purified by polyacrylamide gel electrophoresis prior to immunization. Accordingly this invention provides a method for purifying a glycoprotein, such as the β-subunit of human chorionic gonadotrophin which comprises subjecting the β-hCG subunit to polyacrylamide gel electrophoresis in tubes containing an upper gel and a lower gel suspended in an electrophoretic apparatus having an upper chamber and a lower chamber, said chambers containing buffer solutions, wherein said lower gel and said upper chamber buffer solution both contain a fluorescent probe consisting of the magnesium salt of 8-anilino-1-naphthalene-sulfonic acid referred to hereinafter as ANS, and after terminating the electrophoretic run, cutting out the fluorescent boundaries corresponding to the β-hCG subunit located at the most anodic portion of the gel.

It is to be understood that other glycoprotein antigens and their subunits or subfragments may be purified by the method of this invention. These glycoproteins, besides hCG, would illustratively include human luteinizing hormone, human follicle stimulating hormone, human thyroid stimulating hormone, human menopausal gonadotrophin, pregnant mare's serum gonadotrophin, and carcino embryonic antigen.

Preferably, the lower gel which is the separating gel contains about 5.4% polymerized acrylamide and about 0.5mg percent of ANS. It will be understood by those skilled in the art that the amount of free acrylamide and ANS may vary with the individual glycoprotein hormone which is electrophoresed.

The subunits isolated from the hormone complex reveal 3 components for hCG-α and 5 components for hCG-β.

Besides these glycopeptides it was also found that hCG-β was contaminated by extraneous substances which had the slowest anodic mobility. In addition one cannot exclude the possibility that hCG and its subunit and other glycoprotein hormones were also present in the hCG-β preparation.

In order to circumvent the problem of contamination in hCG-β only material which had an electrophoretic mobility remote from that of other substances was excised from gels and used for immunization.

While an antiserum to the highly purified β-hCG may be produced by many standard methods of immunization it is preferred according to this invention to produce the antiserum by immunizing the host animal in the spleen. Thus, this invention also includes the method of producing an antiserum to a glycoprotein antigen, such as β-hCG, which comprises immunizing the host animal in the spleen. Preferably the antigen utilized for the immunization is the highly purified β-hCG obtained from the polyacrylamide gel electrophesis and the spleen immunization is also followed by subcutaneous injection of the antigen.

The most widely used immunization procedures for the induction of antibodies to proteins and other macromolecules employ foot pad innoculations. This method has a major disadvantage in that the foot pad occasionally becomes infected and necrotic. Furthermore, the disease may become disseminated and prove fatal to the animal, and a costly antigen may be lost. This has not been observed in the case of animals immunized via the splenic route.

The potential use of spleen immunization followed by subcutaneous injection is reflected in the consistently high antibody titers produced to hCG-β in short periods of time. The β-hCG antiserum produced by utilizing the highly purified β-hCG obtained from polyacrylamide gel electrophoresis is highly specific and possesses very low cross reactivity to interfering antigens. Thus, when used as an immunologic reagent preferrably in lyophilized form in hemagglutination test methods, more reliable results are obtained and more sensitive tests can be designed as described in co-pending applicaiton AHP-6522 of Krupey, Hirsch and Irvine filed of even date herewith.

The invention may be further illustrated by reference to the following examples.

STOCK SOLUTIONS

The following stock solutions were prepared in distilled deionized water using the following nomenclature: BIS is N,N'-methylene bis acrylamide; TRIS is tris (hydroxymethylene diamine); TEMED is N,N,N',N'-tetramethylene diamine.

|  | A | B | C | D | E | F |
|---|---|---|---|---|---|---|
| 1N HCl | 48 ml | ~48 ml | — | — | — | — |
| TRIS | 36.6g | 5.98g | — | — | — | — |
| TEMED | 0.23ml | 0.46ml | — | — | — | — |
| Acrylamide | — | — | 21.6g | 10.0g | — | — |
| BIS | — | — | 1.13g | 2.5g | — | — |
| Riboflavin | — | — | — | — | 4mg | — |
| Sucrose | — | — | — | — | — | 40g |
| Water q.s. to | 100ml | 100ml | 100ml | 100ml | 100ml | 100ml |
| pH | 8.9 | 6.7 w/HCl | — | — | — | — |

GEL PREPARAITON

The lower gel was prepared by pouring a fresh folution containing 2.5 ml of A, 5ml of C, 2.5ml of distilled deionized water with an equal volume of ammonium persulfate solution (0.14g/100ml) and 0.1 ml of ANS (1 mg/ml solution of the Mg salt of 1-anilino-8-naphthalene sulfonic acid) into a gel tube having 0.6 cm inner diameter and 9.5 cm in length, the bottom end being temporarily sealed. Water was then layered on top of the solution to eliminate any meniscus. The gel formed after polymerizing for 1/2 hour and excess unpolymerized acrylamide on top was removed by washing with a solution contaiing 1 part B: 2 parts E:6 parts water, and the bottom seal was then removed.

An upper spacer gel was then prepared by layering on top of the lower gel a fresh solution containing 1 ml of B, 2ml of D, 1ml of E and 4ml of F. Water was then layered over the upper gel solution and the gel was then formed by photopolymerization with fluorescent light for 1/2 hour and removing excess water. The lower gel contains about 5.4% of unpolymerized acrylamide and 0.5mg percent of ANS and the upper gel contains about 2.5% unpolymerized acrylamide.

ELECTROPHORESIS

The gel tubes were marked at a distance of 5.5cm from the top of the lower gel. Then, 200ug of the protein (β-hCG, α-hCG, etc.) was layered on the upper spacer gel, the protein solution contains 2mg of protein per ml of 0.15M phosphate buffered saline at pH 7.4 containing 10% dextrose. Tank buffer (0.6g TRIS, 2.88g glycine, 5mg ANS in water q.s. to 1 liter and pH 8.3) was then layered over the sample. The tubes to be electrophoresed were placed in an electrophoretic apparatus having upper and lower chambers for receiving said tank buffer. To 400ml of tank buffer in the upper chamber was added 1ml of 0.001% Bromophenol Blue as a tracking dye. The cathode was contacted to the top of the tube and the anode to the bottom. Electrophoresis was conducted at 4° C. and a current of 2 milliamps per tube was applied till the tracking dye reached the interface of the two gels and then a current of 3 milliamps per tube until the tracking dye reached the 5.5cm mark as described, a total of about 90 minutes. The tubes were removed from the apparatus and the gels were reamed out of the tubes. The portions of the gel, which under long wave UV light corresponded for exmaple, to β-hCG were excised immediately in the form of discs or tablets and frozen to avoid possible diffusion of the protein.

ANALYTICAL STANDARD

For first establishing the location of the β-hCG after conducting the electrophoresis, samples of alpha and beta hCG were electrophoresed as described. The glycoproteins on the gels were then immediately fixed by staining with Amido Schwartz, also known as Buffalo Black (0.2g/100ml of 7% Acetic acid), for 90 minutes, then destained electrophoretically in 7% acetic acid. It was determined that the portions of β-hCG to be excised were in the far anodic regions of the gel.

IMMUNIZATION PROTOCOL

The acrylamide tablets from the ANS stained gels, twelve in number, containing approximately a total of 2.4mg hCG-β were suspended in 4 ml of phosphate buffer 0.15M, pH 7.4 and homogenized for 30 seconds. An equal volume of Freund's adjuvant (complete) was then added and the mixture emulsified. One ml of this emulsion contained approximately 300 micrograms of hCG-β.

White male New Zealand rabbits (2.5–3.0kg) were fasted 16 hours before surgery. The animals were anaesthetized by slow intravenous injection of Nembutal, 60 mg/kg of body weight. Anaesthesia was further continued by ether inhalation until good muscle relaxation was insured.

A left subcostal incision was then made exposing the spleen. The organ was gently grasped with two surgical sterile gauze compresses presoaked in saline at 37° C. The antigen was injected into the spleen using a sterile 1 ml tuberculin syringe with a #20 guage needle. No more than 0.1 ml was injected per location. The total volume injected varied from 0.5 → 1.0 ml depending on the size of the spleen. The incission was closed using 00 silk sutures. The remaining antigen was injected subcutaneously in preshaven areas around the neck. The animal was then given a one milliter injection, intraperitoneal with a suitable antibiotic.

Thirteen days following primary immunization with hCG-β, the animals were bled via the central ear artery using a No. 20 hypodermic needle and the antibody titer determined by microtiter hemagglutination. Each animal then received multiple subcutaneous injections of a total concentration of 300 μg/ml of hCG-β in Freund's adjuvant. This process of subcutaneous immunization and testing of serum extended over a period of 64 days with the immunogen being administered over 10-14 day intervals. Finally, the animals were exsanguinated by cardiac puncture and the antiserum tested for specificity.

We claim:

1. A method for purifying the beta subunit of human chorionic gonatrophin which comprises subjecting the β-hCG subunit to polyacrylamide gel electrophoresis in a tube containing an upper gel and a lower gel suspended in an electrophoretic apparatus having upper and lower buffer chambers wherein both the lower gel and the upper chamber buffer contain a fluorescent probe consisting of the magnesium salt of 8-anilino-1-naphthalene-sulfonic acid terminating the electrophoresis, and cutting out the fluorescent boundaries corresponding to the β-hCG subunit located at the most anodic portion of the gel.

2. The method of claim 1, wherein said lower gel contains about 5.4% polymerized acrylamide.

3. The method of claim 2, wherein the concentration of the fluorescent probe in both the lower gel and upper buffer is about 0.5 milligram percent.

4. The beta subunit of human chorionic gonadotrophin obtained by the method of claim 1.

5. A method for purifying a glycoprotein antigen which comprises subjecting said antigen to polyacrylamide gel electrophoresis in a tube containing an upper gel and a lower gel suspended in an electrophoretic apparatus having upper and lower buffer chambers wherein both the lower gel and the upper chamber buffer contain a fluorescent probe consisting of the magnesium salt of 8-anilino-1-naphthalene-sulfonic acid terminating the electorphoresis, and cutting out the fluorescent boundaries corresponding to said antigens.

* * * * *